United States Patent [19]

Scudder

[11] 4,149,716
[45] Apr. 17, 1979

[54] BIONIC APPARATUS FOR CONTROLLING TELEVISION GAMES

[76] Inventor: James D. Scudder, 420 Rivermont Ave., Lynchburg, Va. 24503

[21] Appl. No.: 809,621

[22] Filed: Jun. 24, 1977

[51] Int. Cl.² .............................................. A63B 71/04
[52] U.S. Cl. .................................. 273/1 E; 128/2.1 B; 273/85 G; 273/DIG. 28
[58] Field of Search ......... 35/22 R; 128/2.08, 2.06 R, 128/2.06 E, 2.1 R, 2.1 B, 2.1 E, 2.1 M, 2.1 Z; 273/1 E, 85 G, DIG. 28

[56] References Cited

U.S. PATENT DOCUMENTS

| | | | |
|---|---|---|---|
| 3,777,410 | 12/1973 | Robinson | 273/85 G X |
| 3,778,058 | 12/1973 | Rausch | 273/85 G |
| 3,896,790 | 7/1975 | Dikmen | 128/2.1 B |
| 3,929,335 | 12/1975 | Malik | 273/DIG. 28 X |
| 3,942,516 | 3/1976 | Glynn et al. | 35/22 R |
| 3,983,865 | 10/1976 | Shepard | 128/2.1 M |
| 3,991,304 | 11/1976 | Hillsman | 128/2.08 X |

OTHER PUBLICATIONS

Radio-Electronics; "Mind Power:Alpha"; Jul. 1976; pp. 36-38, 91.
Radio-Electronics; "Mind Power:Alpha"; Sep. 1976; pp. 49-51, 56.
Popular Electronics; "Alpha Brain Waves & Biofeedback Training"; Dec. 1972; pp. 33-38.

Primary Examiner—Vance Y. Hum
Attorney, Agent, or Firm—Eric P. Schellin

[57] ABSTRACT

An apparatus for controlling electrically operated television games utilizing minute electric signals generated by the firing of neuron impulses in a selected portion of the human body. The minute electric impulses generated by the firing of neurons in the nerve tissue of the human body when a deliberate muscular response is demanded by the human brain are detected by electrodes contacting the exterior skin of the human body in the vicinity of a muscle, amplified, filtered or extraneous signals, suitably conditioned and utilized to control a selected display on a video display screen in response to the voluntarily generated neuron-firing electrical signals.

1 Claim, 4 Drawing Figures

Headband

LM321

LM324

LM358

BIONIC APPARATUS FOR CONTROLLING TELEVISION GAMES

BACKGROUND OF THE INVENTION

Television games, in which special maneuverable and/or controllable displays replace those received from television broadcast stations, for the purpose of playing competitive games, by deliberately manipulating the motion and position of such displays have been described in U.S. Pat. Nos. 3,809,395 to Allison and Greaf, 3,659,285 to Baer, Rusch, and Harrison and 3,829,095 to Baer. These patents disclose the control of visual, movable displays on television or video screens, in the form of various games which can be played. The control means employed by the operators are manually controlled by the operators. Similar games employing video tube displays, in which an operator manipulates manual controls to maneuver his display with reference to a preprogrammed display supplied by video - tape recorder or other device is disclosed in U.S. Pat. No. 3,921,161 to Baer. Improvements to the electronic controls to such games are contained in U.S. Pat. Nos. 4,006,474 to Lukkarilla, and 4,006,898 to Greaf and Price.

Devices for various prosthetic uses to aid in exercising parts of the human body by sensing neuron-firing electric impulses and providing feedback to the human being in a manner appropriate to the objective of the apparatus are described in U.S. Pat. Nos. 3,916,876 to Freeman, 3,641,993 to Gearder and Leaf, and 3,978,847 to Fehmi and Schneider.

Systems for controlling artificial prosthetic devices, such as artificial limbs, utilizing as initial input signals the electrical impulses detected from neuron-firing activity in human tissue, are described in U.S. Pat. No. 3,735,425 to Hoshall, Seamone and Konigsbert.

None of the prior art contemplates, discloses or claims a method of controlling television or video displays which suitably amplify, rectify, reamplify, and regulate the electric impulse received from the neuron firing electric impulse in a fashion suitable for input to a conventional television set through commercially available "game chip" or "chips" for the purpose of deliberately manipulating displays on the television set visual screen according to the electronic circuitry of the "game chip" or "chips".

SUMMARY OF THE INVENTION

The major advantage of the subject invention is to utilize electric impulses, generated by the firing of neurons in human tissue, sometimes called myoelectric impulses, to operate television type displays in game form, rather than by the manual controls before employed. Such games may be played by two or more persons or may be played by one person using two or more of the many possible neuron firing electric impulses locations in the human body. This invention comprises the detection of minute electric neuron discharge voltages, by electrically conducting means removably affixed to the human skin adjacent to muscle or other suitable neuron firing electric impulse generating tissue, amplifying, rectifying, reamplifying and processing these electric signals into operator-selectable linear or digital form suitable for providing electric input to a television set through one or more "game chips" for the purpose of consciously maneuvering or controlling visible displays on the television display tube. One or more operators can then manipulate their selected displays according to rules which may be set forth from time to time consistent with the design of the "game chip" or "chips" through which the inputs are conducted to the television set and thus compete with one another in excellence of maneuvering or controlling displays according to the particular rules and "game chips" or "chips" chosen. Using the same apparatus, one person may manipulate the displays to enable one part of his body to compete with another part, providing both body parts are such that neuron-firing impulses can be detected by the electrically conducting devices attached electrically conductively to the parts of the body selected.

An object of this invention is to enable the manipulation of selected television displays by utilizing neuron-firing electric impulses, rather than utilizing manual control of electric devices, to control visual displays in television display games. Another objective of this invention is to detect electric voltages in the form of voluntary generation of neuron-firing electric impulses in human tissue, and utilizing these signals, suitably detected, amplified, and electronically conditioned in linear or digital form, according to the type of signal required, for input to a television receiver to control or maneuver displays on the video screen.

DESCRIPTION OF A PREFERRED EMBODIMENT

Figure 1:
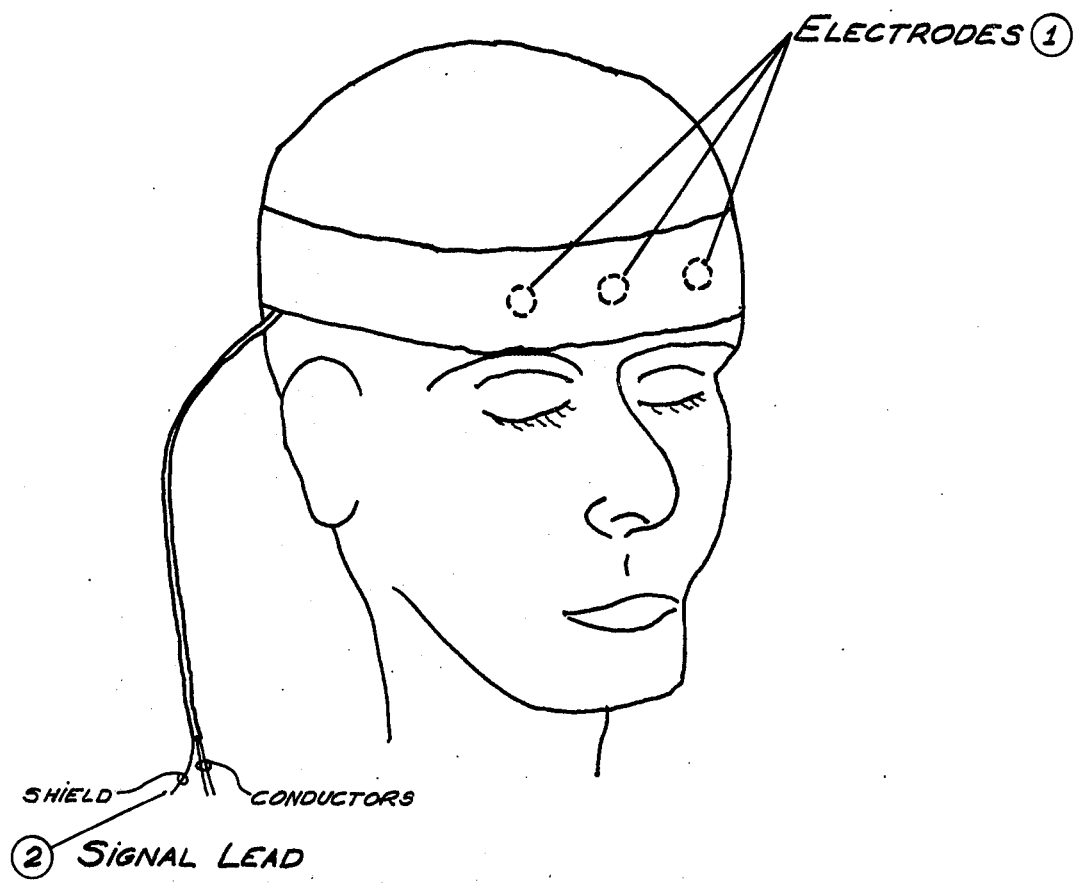
FIG. 1 is a schematic view of the devices utilized for the detection of neuron-firing electric impulses, in this example applied to the head of a human operator, but applicable to any other appropriate part of the human body.
Figure 2:
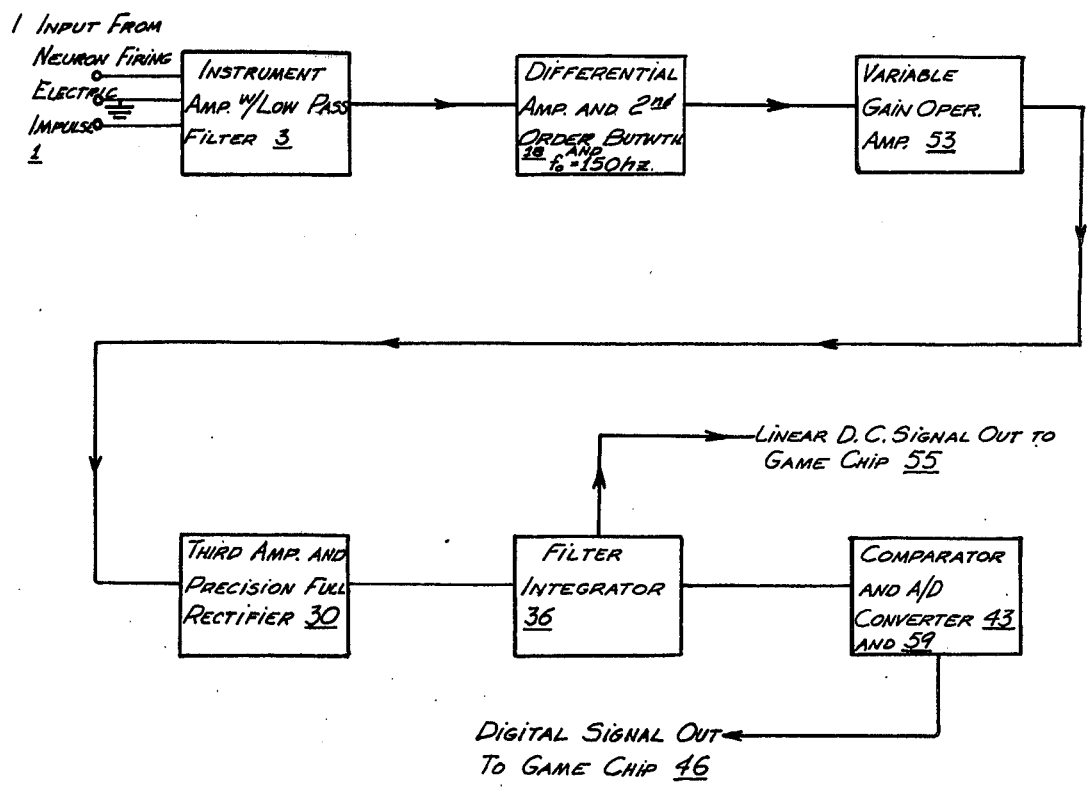
FIG. 2 is a block diagram of the amplification, rectification, signal conditioning and reamplification units utilized to convert the minute neuron-firing electrical impulses detected into signals usable for control of television displays, together with the necessary electrical sensitivity and signal amplitude controls, for electrical input to a "game chip" and/or "chips" (not shown) and a standard television receiving and visual displaying apparatus. (not shown)
Figure 3:
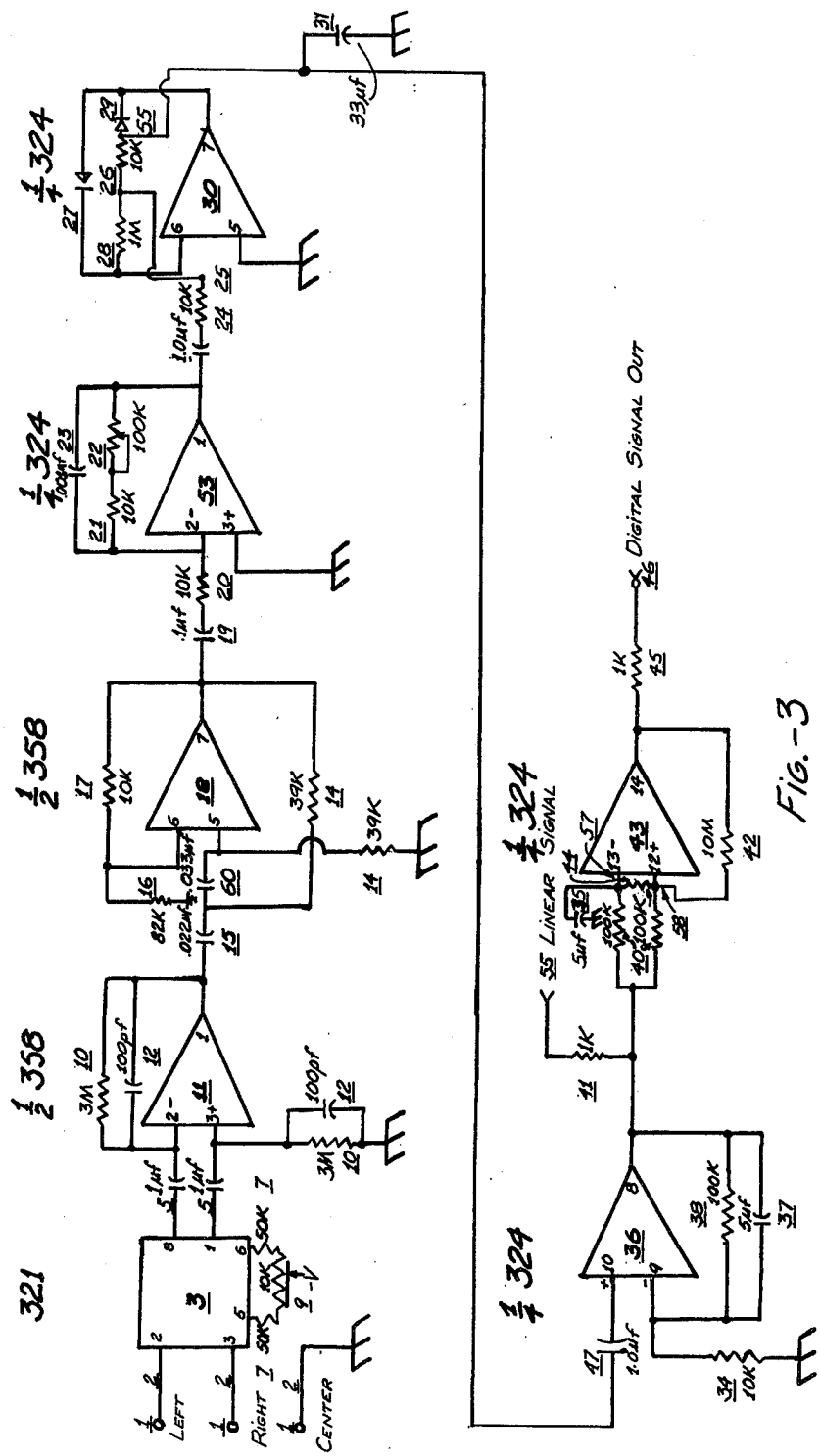
FIG. 3 is a detailed circuit diagram of the electronic circuits as utilized in a preferred embodiment up to the point of connection with a "game chip" or "chips" which further provides input to standard television receiving and visual display apparatus. This figure displays one of two or more identical circuits, each receiving one neuron firing electric impulse (myoelectric) input and controlling one game function or vector. The function of one of these electric amplifying, detecting and conditioning apparatus which is identical to, but electrically separate from other identical detecting, amplifying and conditioning apparatus is described in the description of the preferred embodiment, understanding that other amplifying, detecting, and conditioning apparatus operates identically in response to a separate set of neuron-firing electric impulses.

Referring to the figures, FIG. 1 displays a method of detecting the neuron-firing electric impulses generated by voluntary movement, or attempted movement, of human muscle tissue, by three electrically conductive electrodes 1 in direct physical and electric contact with the human skin, in this example the human head, but not necessarily restricted to, the head, one of which is in an electrically neutral position on the skin in close proximity to selected muscle tissue and connected to the electrical ground of the apparatus as shown in FIGS. 2 and 3 and the other two contacts in proximity to neuron-firing human tissue. The electrodes are mounted in non-electrical conductive material suitable for temporary attachment to human skin adjacent to human muscle tissue or other neuron-firing electrical impulse generating tissue. The neuron-firing electric impulses so generated are typically alternating polarity voltages of a frequency mainly between 90 Hz and 500 Hz, with typical peak amplitudes of between 0.25 microvolts and 250 microvolts. The electric impulses so generated are conveyed to a signal amplifier and additional electronics as shown in FIGS. 2 and 3 electrically by conducting wire 2, preferably of low electrical resistance and suitably shielded from external to the detection apparatus 1 and connecting electrical conductors 2. Two such electrodes 1 and electrically conducting wires 2 are attached physically and electrically, as stated above, to each of two or more operators intending to control or maneuver television screen display by voluntary muscle movement, or attempted movement and a third such electrode 1 is attached physically and electrically symetrically between the aforementioned electrodes to produce an electronically neutral point on each operators skin. It is fully understood and contemplated by this invention that a single person, may, by attaching electrodes as described above in proximity to two chosen muscles or other neuron-firing electric impulse generating tissue may control or maneuver the electronic display by conscious movement, or attempted movement of those chosen muscles or conscious generation of neuron-firing electric impulses in other human tissue.

Referring now to FIG. 3, two connecting wires 2 are connected electrically to the input of first amplifier 3, and a third wire 2 is connected from a neutral point electrically on the skin to the neutral point (ground) of the electronic apparatus. One such amplifier is shown, but it is fully understood and contemplated in this invention that more than one such amplifier may be used, depending on the number of operators controlling their particular displays on the television video display. The electrical outputs of first amplifier 3 are increased in voltage over the input voltage by a factor of approximately 1000. The first amplifier 3 is typically a National Semiconductor Type LM321 integrated circuit chip, detailed circuitry on which chip is shown on FIG. 4 denoted as 3. From the neuron-firing voltage electrode 1 and electric conductors 2 input voltages are connected to terminals 2 and 3 of the LM321 chip 3 as shown. Fixed 50,000 ohm resistors 7 are connected electrically to the fixed ends of a 10,000 ohm potentiometer 9 from terminals 5 and 6 of the LM321 chip. The variable contact of potentiometer 9 is connected electrically to terminal 4 of the LM321 chip 3 which is connected electrically to the negative point of the power supply voltage (not shown). Resistors 7 and potentiometer 9 electrically connected as shown, cooperate to vary the gain of first amplifier output voltage in accordance with movement of the variable contact of potentiometer 9. A voltage supply of between four (4) and twelve (12) volts from a regulated voltage amplitude ripple free direct current power supply (not shown) is connected electrically to terminal 7 and 4 of the LM321 chip 3 with the positive polarity applied to terminal 7 and the negative polarity applied to terminal 4 at the electrical position of the variable arm of potentiometer 9.

The electrically amplified signal from the LM321 chip 3 and associated circuitry described above is connected electrically from the output of first amplifier chip LM321 3 terminals 1 and 8 to one terminal each of two one (1) microfarad condensers 5. The other terminals of condensers 5 are electrically connected to the input terminals 2 and 3 of differential amplifier 11, typically one electrical half of a National Semiconductor integrated circuit chip type LM358. A detailed diagram of the electronic components within, and electrical connections to, this LM358 chip 11 is shown on FIG. 4, designated as 61. The purpose of condensers 5 is to pass alternating current output from the first amplifier 3 to the input terminals of differential amplifier 11, at the same time preventing passage of direct current between the output of the first amplifier 3 and the input of differential amplifier 11 whose function will be described below. As will be observed from FIG. 4, the detailed diagram of the LM358 chip 61 is comprised of two amplifier circuits which when connected as shown in FIG. 3 comprise a differential amplifier. Alternating signal input voltage is electrically connected to the LM358 chip 11 at terminals 2 and 3. The 3 megohm resistors 10, connected as shown in FIG. 3 cooperate to set the gain of the differential amplifier 11. The 100 picofarad concensers 12, connected as shown in FIG. 3, cooperate to lower the gain of the amplifier at higher frequencies especially over 200 Hz. The amplified alternating current signal from the LM358 chip 11 is electrically coupled to terminal 5 of LM358 chip 61 through capacitors 15 and 60 providing electrical input to high pass filter amplifier 18. High pass filter amplifier 18 is typically one half of National Semiconductor integrated circuit chip LM358 61. The 0.02 microfarad condenser 15, the 0.033 microfarad condenser 60 and the 39,000 ohm resistors 14 electrically connected as shown in FIG. 3, cooperate to set the center amplification frequency of the High Pass filter amplifier 18 at approximately 150 Hz. The 10,000 ohm resistor 17 and the 8200 ohm resistor 16, electrically connected to Pin 6 of High Pass filter amplifier 18 as shown in FIG. 3, cooperate to set the overall "Q" factor or gain of the High Pass filter amplifier 18 at an optimum value of 30 to 60. The overall voltage gain from input signals detected by electrodes 1 to the output of High Pass filter amplifier 18 is approximately 1500 in the frequency pass band.

Power is supplied to differential amplifier 11 and high pass filter amplifier 18 from a regulated, four (4) to twelve (12) volt ripple voltage free direct current power source (not shown) with negative polarity electrically connected to terminal 4 and positive polarity electrically connected to terminal 8, both on chip LM358 61 as shown in FIG. 3.

The purpose of the differential amplifier 11, and High Pass filter amplifier 18 and interconnected electronics described above, is to amplify differences in amplitude of the two voltages detected from the electrodes relative to the ground potential of the electronic apparatus, as amplified by the first amplifier 3. The differential amplification so accomplished filters and reduces electronic noise and partially conditions the voltage signal by rejecting undesirable frequencies and "smoothing" the desired, amplified voltage signals. "Smoothing" electrical signals is intended to mean the reduction of sharp increase and decrease in voltage with respect to time, thus providing a substantially "smoother" voltage profile.

Figure 4:
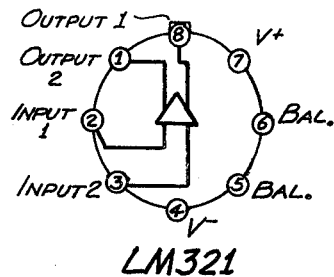
FIG. 4 is a more detailed set of diagrams of the solid-state electronic circuitry contained in the several integrated circuits referred to in the specification.
Figure 4:
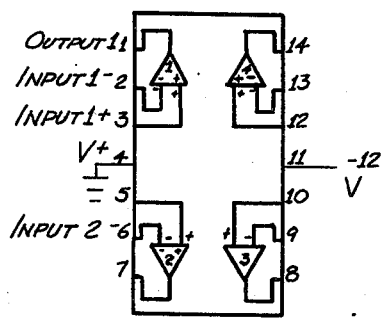
Figure 4:
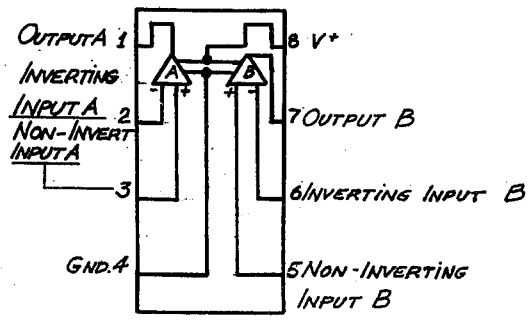

The "smoothed" and filtered alternating polarity electrical voltage signal output from the differential amplifier 11 and filter amplifier 18 is electrically connected to the input on a second amplifier 53 through 0.1 microfarad condenser 19, which prevents passage of direct current voltage signals but permits passage of alternating current voltage signals, and through a 10,000 ohm resistor 20, the purpose of which will be stated further in this description. Second amplifier 53 is typically one of four amplifiers contained in a National Semiconductor integrated circuit chip LM324, 54. A more detailed showing of the interior electronics of chip LM324 54 is shown in FIG. 4. It will be seen that this chip contains four (4) separate and independent amplifier circuits, provided with a common power supply of four (4) to twelve (12) volts from a direct current, regulated and voltage ripple free power supply (not shown) with the negative polarity electrically connected at terminal 11, and the positive polarity electrically connected to terminal 4 and to electrical ground. This power input provides electric power for all four amplifier circuits contained in the LM324 54 chip. Each amplifier circuit of the LM324 chip typically can amplify the voltage input by a factor of 1000. 10,000 ohm resistor 21 and 100,000 ohm potentiometer 22 cooperate when connected as shown in FIG. 3 to provide an amplification control of the output signal from the second amplifier 53. By adjusting the position of the variable contact on potentiometer 22 the gain of the second amplifier 53 may be varied, thus adjusting the amplitude of the output voltage, and subsequently the signal supplied to and through a "game chip" or "chips" to the television set, to modify the display on the television set video screen to suit the human operator manipulating the display and consistent with the display arranged on the video screen by the "game chip" electronic circuitry. The 0.001 microfarad condenser, 23 connected as shown in FIG. 3 is included to cause high frequency amplification decrease in second amplifier 53, thus causing the amplification at frequencies over 1500 Hz to be progressively decreased as frequency increases. Output of the second amplifier 53 is electrically connected to another of the four amplifier circuits in the LM324 54 integrated circuit chip 30, through 1 microfarad condenser 24 which permits passage of alternating voltage signals, and prevents passage of direct current, between second amplifier 53 and the input of the third amplifier rectifier circuit 30 to which it is connected. The third amplifier rectifier circuit 30, the 1 microfarad condenser 24, the 10,000 ohm resistor 25, the one megohm resistor 28, the 10,000 ohm resistor 26 and diodes 27 and 29, connected as shown in FIG. 3, cooperate to form a precision linear full wave alternating current rectifier, capable of converting the alternating current input from second amplifier 53 into pulsating direct current voltage, which pulsations vary in amplitude linearly throughout their amplitude range, down to zero volts, proportionate to the magnitude of the "smoothed" alternating current voltage impulses received from second amplifier 53. Condenser 31, as shown in FIG. 3, bypasses any pulsating direct current frequency higher than three hundred (300) cycles per second to ground, as such frequencies are both unwanted and unnecessary in controlling the television set display.

The pulsating DC electrical signal from amplifier rectifier 30, at circuit node 55, is electrically coupled through a 1.0 microfarad capacitor 47, to fourth amplifier 36, of the four units in the LM324 integrated circuit chip 54. The one (1) microfarad capacitor 47 blocks any buildup of direct current voltage from third amplifier-rectifier 30 from fourth amplifier 36, thus minimizing voltage offset and drift. 10,000 ohm resistor 34, 100,000 ohm resistor 38 and 5 microfarad capacitor 37 connected as shown in FIG. 3 to fourth amplifier 36 form an integration circuit, which provides a smooth direct current output proportional to the amplitude of the pulses received from amplifier-rectifier 30. The electrical output of fourth amplifier 36 is divided into two electrical paths. The first electrical path is connected electrically through 1,000 ohm resistor 41 which serves as a ballast (current limiting) resistor to the linear D.C. output terminal of the apparatus 55. This output is applied to a switching matrix (not shown) controlled by the operator to provide the game rules for the selected "game chip" or "chips" and then to the proper "game chip" inputs (not shown) when linear D.C. electric input is required for said input. This linear D.C. output further provides the linear control response, to which the action of the selected display on the television screen responds, in direct, linear proportion to the degree of neuron firing being generated consciously by the operator.

The second electrical path is connected electrically into the two 10,000 ohm resistors 40, connected as shown in FIG. 3. These resistors 40 and the fifth amplifier 43, also one-fourth of the LM324 integrated circuit chip 59 form a comparator circuit when electrically connected as shown in FIG. 3. The comparator has only two outputs, high or low, depending on the voltage relationship between its two inputs, thus, it has a "digital" output. One input is called the inverting (−) input while the other is called the non-inverting (+) input. Inverting means the output will be 180° out of phase with the input while non-inverting means the output will be in phase with the input. When the non-inverting input is at or below the potential of the inverting input, the output will be low. If the non-inverting input of pin 12 of fifth amplifier 43 as shown in FIG. 3 increases in potential over the inverting input, pin 13 of fifth amplifier 43, the voltage output will rise substantially instantaneously to a high voltage state. The 10 megohm resistor 42 connected as shown in FIG. 3 forms a hysteresis feedback circuit which makes the comparator less sensitive to small changes in input. The 5 microfarad capacitor 35 connected as shown in FIG. 3 to the inverting input pin 13 of fifth amplifier 43 serves to delay the signal reaching the electric circuit node 57. This serves to cause any sudden change in output of fourth amplifier 36 to reach node 58 before reaching circuit node 57, thus triggering the comparator into producing a high output. This output stays high until voltage at circuit node 57 becomes equal to or less than voltage at circuit node 58 at which time the comparator voltage reverts substantially instantaneously to the low state. 10,000 ohm resistor 44 tends to control the voltage reversion action to the degree needed for the video display action. This is a digital output which when exceeding a preset limit indicates loss of control of neuron-firing on the part of the operator which results in an unplanned change in the video display. This signal is electrically connected through 1000 ohm resistor 45 to circuit output node 46. Comparator high output may be varied by changing the values of resistor 44 and capacitor 35 to vary the preset high output triggering point of the comparator. The digital voltage signal is electrically connected to a switching matrix (not shown) to allow the operator to select the game rules he wishes to play should the "game chip" or "chips" require digital voltage input. The digital signal is is then applied through switching the matrix according to the rules of the game selected to the input of the aforementioned "game chip" or "chips" (not shown) thus influencing the action of the display on the television screen. Another purpose of this digital signal, in addition to providing digital voltage output as indicated above, is to indicate on the television video screen loss of neuron firing control by the operator over a preset rate or exceeding a preset rate of change, with time, set by resistor 49 and capacitor 35 connected as shown in FIG. 3, in the neuron firing rate of the operator with respect to time, demonstrating lack of proficiency in the selected "game" until the operator voluntarily alters his rate or rate of change of neuron firing to below the degree permitted by the circuitry.

When an operator first uses this entire apparatus described above to control television set display in "game" form, his reactions are not normally under very good control. At this time, the second amplifier 53 gain control, potentiometer 22 would be set at a low sensitivity, thus allowing control by gross or large muscle or other neuron firing effort, i.e., large neuron firing levels. As the player gains experience with the system, he can increase the sensitivity of the game and control the displays on the TV screen with much more subtle muscular or other neuron-firing effort and much lower levels of neuron firing. At the most sensitive position of potentiometer 22, only a very minute level of neuron firing is necessary for complete control of the game.

Depending on the output desired from the above described electronic apparatus for the particular "game" being played, either digital or linear voltage signals may be selected. The selection is made by manipulating a game selector switching matrix control (not shown).

Amplified, rectified and linearized or digitized electrical signals from each source of signal amplification circuitry, proportional to the neuron-firing electric impulses generated by the operator, detected, amplified, rectified and conditioned as described above are electrically connected through a manually operated game selector switching matrix (not shown) to a standard "game chip" or "chips" typically, but not necessarily, a General Instrument Co. Series 8500 "game chip" (not shown) which converts the signals so received into signals directing television video displays (not shown) in various "games" as designed into the internal electronic circuitry of the "game chip". The output from the "game chip" or "chips" is connected to the ordinary antenna terminals of a conventional, commercial television set, (not shown) permitting one or more signal operators to manipulate visual display on the television video screen, according to selected maneuvers permitted by "game chip" circuitry.

It is fully understood and contemplated that the term "game chip" as employed in this specification encompasses the electronic circuitry, whether in integrated circuit "chip" form, or other electronic circuitry, which converts incoming electric signals to specific, selectable signals suitable for producing a controllable display on a television video screen, according to the contained electronic circuitry of the "chip", when connected to the antenna terminals of said television set.

It is expected that numerous further modifications to provide for different displays on the television receiver video screen will suggest themselves to those of ordinary skill in the art, and accordingly the scope of the present invention is to be measured only by that of the appended claim.

What is claimed is:

1. Video game input apparatus for controlling and introducing by electrical connections electric signal input into prior art electric circuitry "game chips", the electric signal output of said "game chips" producing video display action on a television set video screen according to the interior electric circuitry of said "game chips" when electrically connected to said television set, by said input apparatus detecting and electrically processing neuron-firing electric impulses generated in human tissue by voluntary direction to the said human tissue by the brain of the operator, comprising:
   means for detecting said neuron-firing electric impulses generated in human tissue;
   means for amplifying the detected electric impulses;
   low pass filter means, having a cut-off frequency of between 150 and 200 hertz, for filtering the amplified impulses and for transmitting those components of the amplified pulses which are lower in frequency than the cut-off frequency, said low pass filter means comprising capacitive coupling means for blocking transmission of the direct current component of said amplified impulses;
   rectifier means for rectifying the filtered impulses;
   integrator means, responsive to the output of said rectifier means, for supplying a first output signal which varies with the time integral of the output of said rectifier;
   comparator means, having hysteresis properties, responsive to said first output signal for supplying a second output signal, said second output signal having either a high or low state, depending upon whether the first output signal is, respectively, increasing or decreasing for a time period and at a rate sufficient in combination to overcome the hysteresis properties;
   means for selectively connecting said first output signal and said second output signal to the said "game chips" as an electrical input thereto;
   the electrical output of said "game chips" being electrically connected to the electric input terminals of said television set;
   whereby the said video display action on said television set video screen is controlled, in accordance with the selective connection of said first and second output signals to said "game chips" and in accordance with the internal game rules of said "game chip", by the voluntary and involuntary generation of neuron-firing of said electric impulses by said operator.

* * * * *